(12) United States Patent
Bhat et al.

(10) Patent No.: US 7,576,093 B2
(45) Date of Patent: Aug. 18, 2009

(54) METHOD OF TREATMENT OF BONE-RELATED DISORDERS OR CONDITIONS

(75) Inventors: Ratan Bhat, Södertälje (SE); Anna-Lena Berg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 157 days.

(21) Appl. No.: 11/683,458

(22) Filed: Mar. 8, 2007

(65) Prior Publication Data
US 2007/0213322 A1 Sep. 13, 2007

Related U.S. Application Data

(60) Provisional application No. 60/780,252, filed on Mar. 8, 2006.

(51) Int. Cl.
*A61K 31/505* (2006.01)
(52) U.S. Cl. ..................................................... 514/275
(58) Field of Classification Search ................. 514/275
See application file for complete search history.

(56) References Cited

U.S. PATENT DOCUMENTS

| | | |
|---|---|---|
| 2003/0176484 A1 | 9/2003 | Day-Lollini et al. |
| 2005/0054663 A1 | 3/2005 | Bennett et al. |
| 2006/0252045 A1 | 11/2006 | Moitreyee et al. |

FOREIGN PATENT DOCUMENTS

| | | |
|---|---|---|
| WO | 0157022 A | 8/2001 |
| WO | 03/004472 | 1/2003 |
| WO | 03057202 A | 7/2003 |
| WO | 03076442 A | 9/2003 |
| WO | 2005027883 A | 3/2005 |
| WO | 2005039485 A | 5/2005 |

OTHER PUBLICATIONS

Johansen et al., Medline Abstract of Drugs & Aging (Feb. 1996), vol. 8, No. 2, pp. 113-125.*
Frost, Medline Abstract of Medicina, (1997), vol. 57, Suppl. 1, pp. 116-126.*
Boyle, Medline Abstract of Balilliere's clinical rheumatology, (Oct. 1993), vol. 7, No. 3, pp. 515-534.*
Albrektsson, T., Brånemark P-I et al, "Osseointegrated Titanium Implants", Acta Orthop. Scand. 1981, 52, pp. 155-170.
Bain, G. et al, "Activated β-catenin induces osteoblast differentiation of C3H10T1/2 cells and participates in BMP2 mediated signal transduction", Biochemical and Biophysical Research Communications 2003, 301, pp. 84-91.
Bell, N.H., "Advances in the Treatment of Osteoporosis", Current Drug Targets—Immune, Endocrine & Metabolic Disorders, 2001, vol. 1, No. 1, pp. 93-102.
Broulik, P.D. et al, "Alterations in human serum alkaline phosphatase and its bone isoenzyme by chronic administration of lithium", Clinica Chimica Acta, 1984, 140, pp. 151-155.

Smith, E. et al, "Glucocorticoids Inhibit Cell Cycle Progression in Differentiating Osteoblasts via Glycogen Synthase Kinase-3β", The Journal of Biological Chemistry 2002, vol. 277, No. 20, May 17, pp. 18191-18197.
Kapadia et al, "Glycogen Synthase Kinase 3 Controls Endochondral Bone Development: Contribution of Fibroblast Growth Factor 18", Developmental Biology, 2005; 496-507, 285.
Kulkarni et al. "Orally Bioavailable GSK3 alpha/beta Dual Inhibitor Increases Markers of Cellular Differentiation in-vitro and Bone Mass in-vivo"; Journal of Bone and Mineral Research 2006; 910-920, 21(6).
Tobias et al "Novel Therapeutic Targets in Osteoporosis"; Expert Opinion on Therapeutic Targets; 2002; 41-56, 6(1).
Skoglund et al; "Simvastatin Improves Fracture Healing in Mice"; Journal of Bone and Mineral Research; 2002; 2004-2008, 17.
Abdul et al; "Inhibiting Glycogen Synthase Kinase-3 (GSK-3) Prevents the Development of Myeloma Bone Disease"; Abstract No. 008. Cancer and Bone Society meeting in Sydney in Mar. 2009.
Brandstrom et al; "GSK-3 Inhibition Increases Trabecular Bone Mass in Mice"; American Society for Bone Mineral Research Annual Meeting; 2006; Abstract No. SA396.
Gong et al; "LDL Receptor-Related Protein 5 (LRP5) Affects Bone Accrual and Eye Development"; Cell; 2001; 513-523, 107.

(Continued)

*Primary Examiner*—Raymond J Henley, III
(74) *Attorney, Agent, or Firm*—Kenneth F. Mitchell

(57) ABSTRACT

The present invention relates to a new use of a compound of the formula (I)

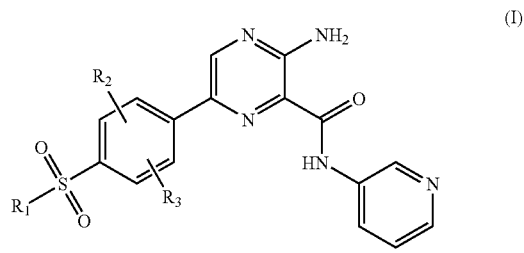

wherein $R_1$ is $NH_2$, piperazin-1-yl, 4-methylpiperazin-1-yl, 4-methyl-1,4-diazepan-1-yl or 4-ethylpiperazin-1-yl;
$R_2$ is hydrogen, fluoro, $CH_3$, $CH_2CH_3$, $OCH_3$, $CF_3$ or $OCF_3$;
$R_3$ is hydrogen, $CH_3$ or fluoro;
as a free base or a pharmaceutically acceptable salt thereof, in the manufacture of a medicament for the prevention and/or treatment of bone-related disorders, osteoporosis and increasing bone formation, bone mineral density. The present invention further relates to a method of prevention and/or treatment of these disorders.

14 Claims, 3 Drawing Sheets

OTHER PUBLICATIONS

Boyden et al; "High Bone Density Due to a Mutation in LDL-Receptor-Related Protein 5"; The New England Jnl of Medicine; 2002; 1513-1521; 346(20).

Little et al; "A Mutation in the LDL Receptor-Related Protein 5 Gene Results in the Autosomal Dominant High-Bone-Mass Trait"; American Jnl of Human Genetics; 2002; 11-19, 70.

Van Wesenbeeck et al; "Six Novel Missense Mutations in the LDL Receptor-Related Protein 5 (LRP5) Gene in Different Conditions with an Increased Bone Density"; American Jnl of Human Genetics; 2003; 763-771; 72.

Bennett et al; "Regulation of Osteoblastogenesis and Bone Mass by Wnt10b"; PNAS; 2005; 3324-3329; 102(9).

Bennett et al; "Regulation of Wnt Signaling during Adipogenesis"; The Jnl of Biological Chemistry; 2002; 30998-31004; 277(34).

Gregory et al; "How Wnt Signaling Affects Bone Repair by Mesenchymal Stem Cells from the Bone Marrow"; New York Academy of Sciences; 2005; 97-106; 1049.

Ross et al; "Inhibition of Adipogenesis by Wnt Signaling"; Science; 2000; 950-953; 289.

Day et al; "Wnt/(3-Catenin Signaling in Mesenchymal Progenitors Controls Osteoblast and Chondrocyte Differentiation during Vertebrate Skeletogenesis"; Developmental Cell; 2005; 739-750; 8.

Hill et al; "Canonical Wnt/(3-Catenin Signaling Prevents Osteoblasts from Differentiating into Chondrocytes"; Developmental Cell; 2005; 727-738; 8.

Clement-Lacroix et al; "Lrp5-Independent Activation of Wnt Signaling by Lithium Chloride Increases Bone Formation and Bone Mass in Mice"; PNAS; 2005; 17406-17411; 102(48).

Tian et al; "The Role of the Wnt-Signaling Antagonist DKK1 in the Development of Osteolytic Lesions in Multiple Myeloma"; The New England Jnl of Medicine; 2003; 2483-2494; 349(26).

* cited by examiner

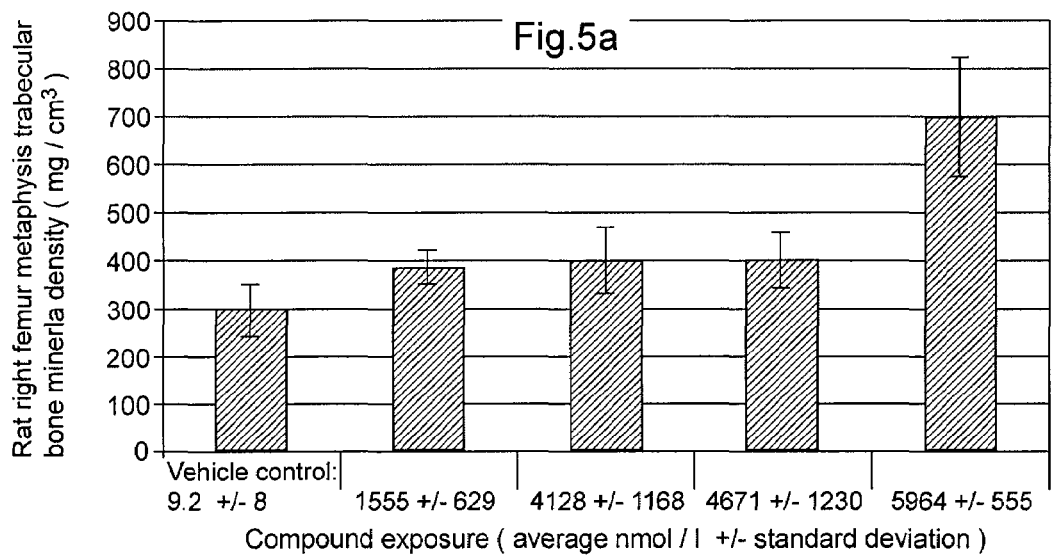
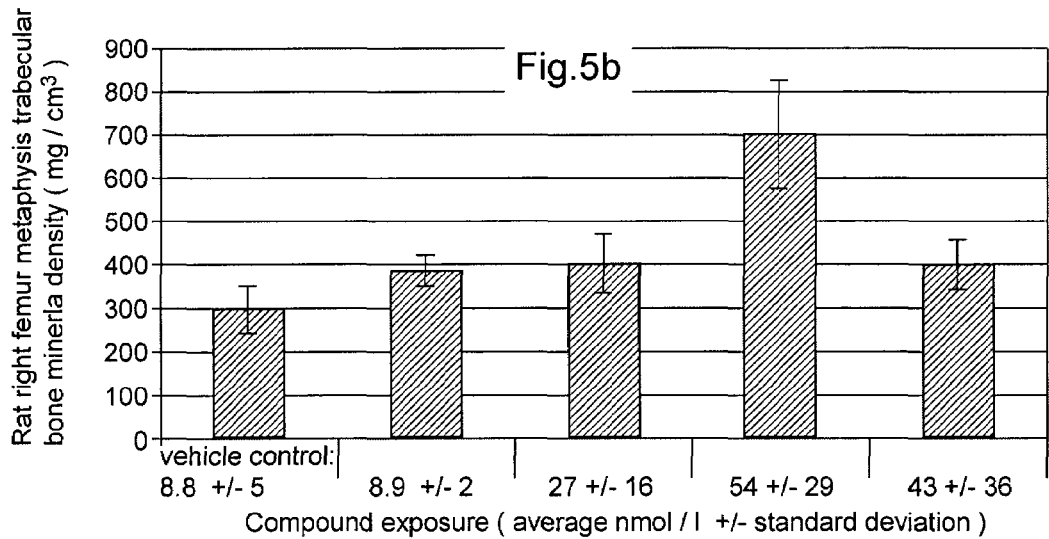
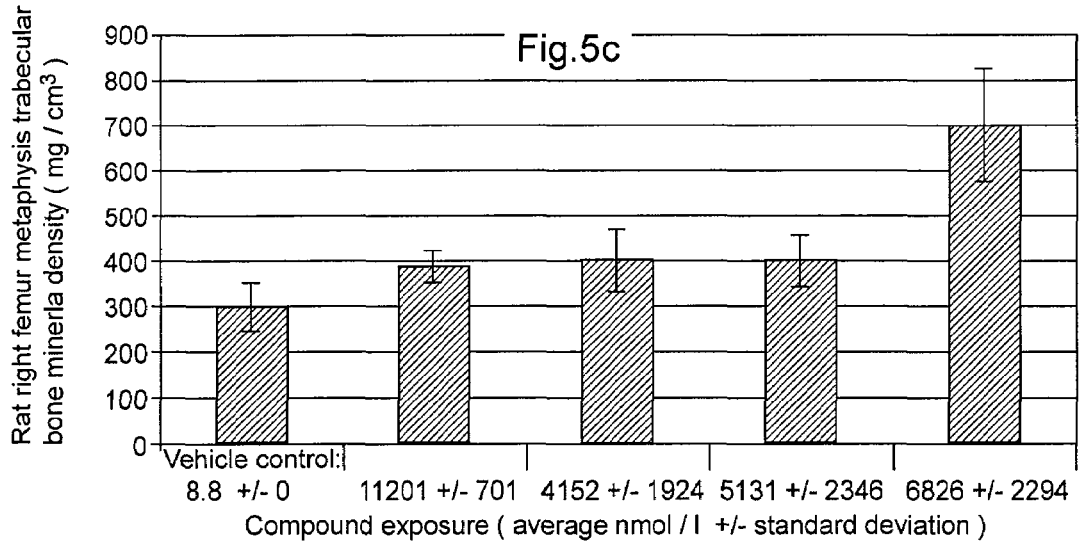

METHOD OF TREATMENT OF BONE-RELATED DISORDERS OR CONDITIONS

FIELD OF THE INVENTION

The present invention relates to a new use of certain GSK3 inhibitors, namely 3-amino-6-{4-substituted)sulfonyl]phenyl}-N-pyridin-3-ylpyrazine-2-carboxamides in the manufacture of a medicament for the treatment and/or prevention of bone-related disorders or conditions, such as osteoporosis and increased bone formation and bone mineral density. The present invention further relates to a method of treatment and/or prevention of these disorders.

BACKGROUND OF THE INVENTION

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on the serine 9 residue and inactivates it.

GSK3 and Bone Disorders

Remodeling of the skeleton is a continuous process, controlled by systemic hormones such as parathyroid hormone (PTH), local factors (e.g. prostaglandin $E_2$), cytokines and other biologically active substances. Two cell types are of key importance: osteoblasts (responsible for bone formation) and osteoclasts (responsible for bone resorption). Via the RANK, RANK ligand and osteoprotegerin regulatory system these two cell types interact to maintain normal bone turnover (Bell N H, *Current Drug Targets—Immune, Endocrine & Metabolic Disorders*, 2001, 1:93-102).

Osteoporosis is a skeletal disorder in which low bone mass and deterioration of bone microarchitecture lead to increased bone fragility and fracture risk. To treat osteoporosis, the two main strategies are to either inhibit bone resorption or to stimulate bone formation. The majority of drugs currently on the market for the treatment of osteoporosis act to increase bone mass by inhibiting osteoclastic bone resorption. It is recognized that a drug with the capacity to increase bone formation would be of great value in the treatment of osteoporosis as well as having the potential to enhance fracture healing in patients.

Recent in vitro studies suggest a role of GSK3$\beta$ in osteoblast differentiation. First, it has been shown that glucocorticoids inhibit cell cycle progression during osteoblast differentiation in culture. The mechanism behind this is activation of GSK3$\beta$ in osteoblasts, resulting in c-Myc down-regulation and impediment of the $G_1$/S cell cycle transition. The attenuated cell cycle and reduced c-Myc level are returned to normal when GSK3$\beta$ is inhibited using lithium chloride (Smith et al., *J. Biol. Chem.*, 2002, 277:18191-18197). Secondly, inhibition of GSK3$\beta$ in the pluripotent mesenchymal cell line C3H10T1/2 leads to a significant increase in endogenous $\beta$-catenin signaling activity. This, in turn, induces expression of alkaline phosphatase mRNA and protein, a marker of early osteoblast differentiation (Bain et al., *Biochem. Biophys. Res. Commun.*, 2003, 301:84-91).

Published in vivo data confirming the in vitro effects of GSK3$\beta$ on osteoblast differentiation are still lacking. However, studies by the inventors clearly show an increased bone formation in rats treated with a GSK3$\beta$ inhibitor (see below under Examples). It should also be noted that patients treated with lithium have increased levels of bone-specific alkaline phosphatase, indirectly providing support for the notion that inhibition of GSK3$\beta$ would lead to osteoblast stimulation and increased bone formation (Broulik et al., *Clinica Chemica Acta*, 1984, 140:151-155).

Figure 1B:
FIG. 1b shows a marked increase in formation of osteoid in the same area of the femur in a rat treated with 60 mmol/kg of 3-amino-6-[4-(4-methylpiperazin-1-yl)sulfonylphenyl]-N-pyridin-3-ylpyrazine-2-carboxamide for 4 weeks. (magnification: ×100).
Figure 2:
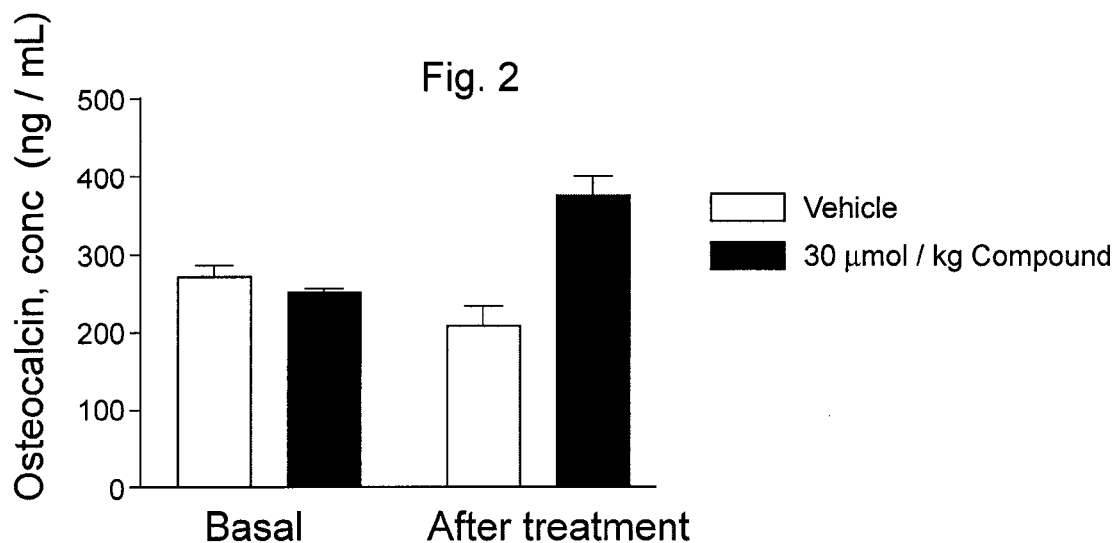
Figure 3:
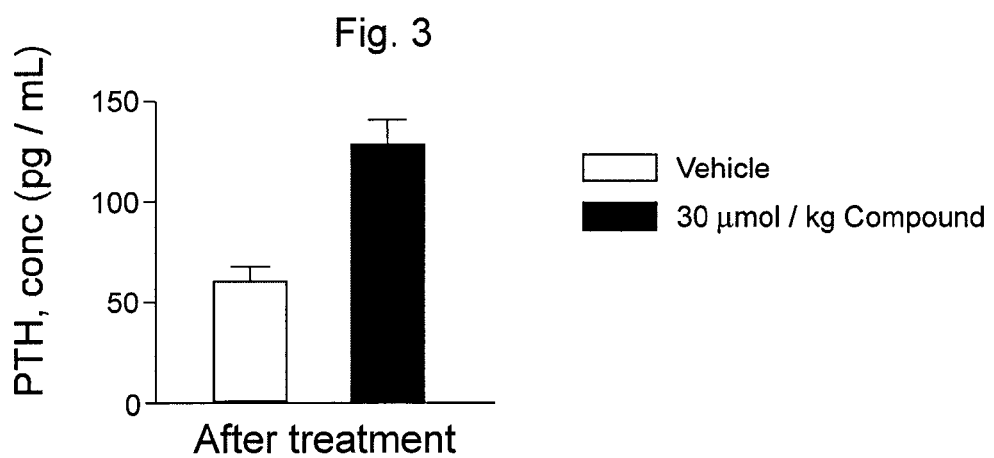
Figure 4:
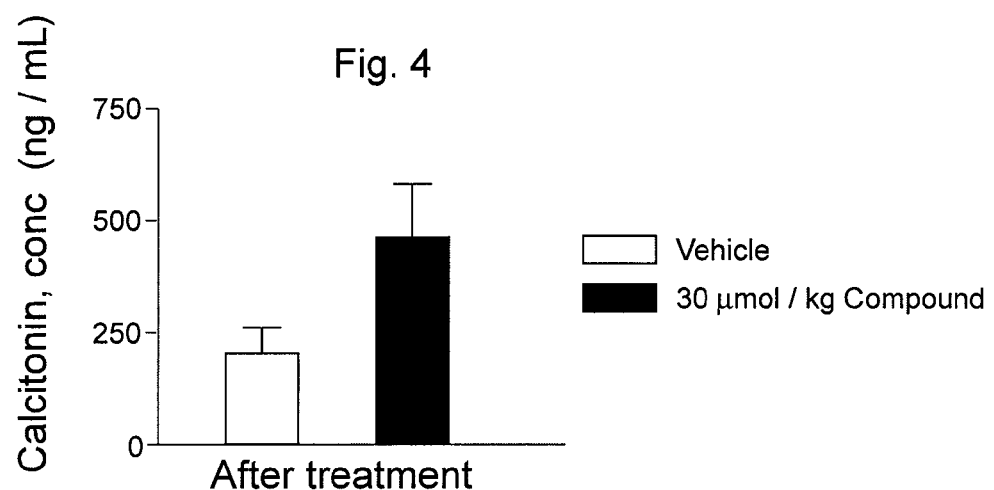

Osteocalcin as well as PTH and calcitonin plasma levels were significantly increased in the drug-treated rats (FIGS. 2-4). The increased PTH and calcitonin levels reflect the need for calcium in the mineralisation of the newly formed bone. Histopathologically, increased bone formation of a similar character as previously observed (Example 1, FIG. 1b) was present in the drug-treated rats.

The results are shown in FIG. 5a, that shows the BMD increases (bone mineral density increases) in mg per cubic centimeter on the Y-axis, that occur in the trabeculae of the right femur metaphysis. The X axis displays the plasma concentrations (+/−Standard Deviation) of 3-amino-6-[4-(4-methylpiperazin-1-yl)sulfonylphenyl]-N-pyridin-3-ylpyrazine-2-carboxamide.

The effect of the compound 3-amino-6-(4-piperazin-1-ylsulfonylphenyl)-N-pyridin-3-ylpyrazine-2-carboxamide on the bone mineral density (BMD) was measured in rat plasma in nM in an analogous way as described in Example 3 above. The results are shown in FIG. 5b, that shows the BMD increases (bone mineral density increases) in mg per cubic centimeter, that occur in the trabeculae of the right femur metaphysic.

The effect of the compound 3-amino-N-pyridin-3-yl-6-(4-sulfamoylphenyl)pyrazine-2-carboxamide on the bone mineral density (BMD) was measured in rat plasma in nM in an analogous way as described in Example 3 above. The results are shown in FIG. 5c, that shows the BMD increases (bone mineral density increases) in mg per cubic centimeter, that occur in the trabeculae of the right femur metaphysic.

DETAILED DESCRIPTION OF THE INVENTION

The present invention is directed to the use of a compound of the formula (I)

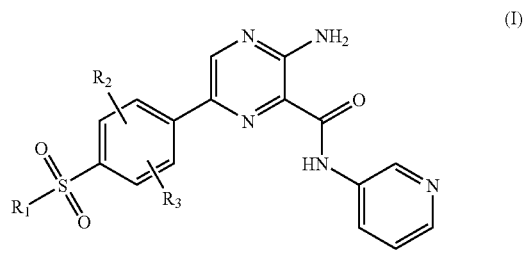

(I)

wherein $R_1$ is $NH_2$, piperazin-1-yl, 4-methylpiperazin-1-yl, 4-methyl-1,4-diazepan-1-yl or 4-ethylpiperazin-1-yl;

$R_2$ is hydrogen, fluoro, $CH_3$, $CH_2CH_3$, $OCH_3$, $CF_3$ or $OCF_3$;
$R_3$ is hydrogen, $CH_3$ or fluoro;

as a free base or a pharmaceutically acceptable salt thereof, for the manufacture of a medicament for use in the treatment and/or prevention of bone-related disorders or conditions.

One aspect of the invention is directed to the use of a compound of the formula (I), wherein $R_1$ is $NH_2$, piperazin-1-yl or 4-methylpiperazin-1-yl, $R_2$ is hydrogen and $R_3$ is hydrogen as a free base or a pharmaceutically acceptable salt thereof, for the manufacture of a medicament for use in the treatment and/or prevention of bone-related disorders or conditions.

One aspect of the invention is directed to the use of a compound of the formula (I), which is 3-amino-6-[4-(4-methylpiperazin-1-yl)sulfonylphenyl]-N-pyridin-3-ylpyrazine-2-carboxamide, 3-amino-6-(4-piperazin-1-ylsulfonylphenyl)-N-pyridin-3-ylpyrazine-2-carboxamide or 3-amino-N-pyridin-3-yl-6-(4-sulfamoylphenyl)pyrazine-2-carboxamide, as a free base or a pharmaceutically acceptable salt thereof, for the manufacture of a medicament for use in the treatment and/or prevention of bone-related disorders or conditions.

The uses of the following named compounds of the formula (I) are also included in the present invention, 3-amino-6-[2,5-difluoro-4-(4-methylpiperazin-1-yl)sulfonyl-phenyl]-N-pyridin-3-yl-pyrazine-2-carboxamide;
3-amino-6-[3-ethyl-4-(4-methylpiperazin-1-yl)sulfonyl-phenyl]-N-pyridin-3-yl-pyrazine-2-carboxamide;
3-amino-6-[3-fluoro-4-(4-methylpiperazin-1-yl)sulfonyl-phenyl]-N-pyridin-3-yl-pyrazine-2-carboxamide;
3-amino-6-[3-methyl-4-(4-methylpiperazin-1-yl)sulfonyl-phenyl]-N-pyridin-3-yl-pyrazine-2-carboxamide;
3-amino-6-[2-methyl-4-(4-methylpiperazin-1-yl)sulfonyl-phenyl]-N-pyridin-3-yl-pyrazine-2-carboxamide;
3-amino-6-[4-(4-methylpiperazin-1-yl)sulfonyl-3-(trifluoromethoxy)phenyl]-N-pyridin-3-yl-pyrazine-2-carboxamide;
3-amino-6-[4-(4-methylpiperazin-1-yl)sulfonyl-2-(trifluoromethyl)phenyl]-N-pyridin-3-yl-pyrazine-2-carboxamide;
3-amino-6-[5-fluoro-2-methyl-4-(4-methylpiperazin-1-yl)sulfonyl-phenyl]-N-pyridin-3-yl-pyrazine-2-carboxamide;
3-amino-6-[2,5-dimethyl-4-(4-methylpiperazin-1-yl)sulfonyl-phenyl]-N-pyridin-3-yl-pyrazine-2-carboxamide;
3-amino-6-[2-fluoro-4-(4-methylpiperazin-1-yl)sulfonyl-phenyl]-N-pyridin-3-yl-pyrazine-2-carboxamide;
3-amino-6-[4-(4-ethylpiperazin-1-yl)sulfonylphenyl]-N-pyridin-3-yl-pyrazine-2-carboxamide and
3-amino-6-[4-[(4-methyl-1,4-diazepan-1-yl)sulfonyl]phenyl]-N-pyridin-3-yl-pyrazine-2-carboxamide, as a free base or a pharmaceutically acceptable salt thereof.

One aspect of the invention is directed to the use of a compound of the formula (I), as a free base or a pharmaceutically acceptable salt thereof, to treat osteoporosis.

One aspect of the invention is directed to the use of a compound of the formula (I), as a free base or a pharmaceutically acceptable salt thereof, to increase and promote bone formation in mammals.

One aspect of the invention is directed to the use of a compound of the formula (I), as a free base or a pharmaceutically acceptable salt thereof, to increase bone mineral density in mammals.

Another aspect of the invention is directed to the use of a compound of the formula (I), as a free base or a pharmaceutically acceptable salt thereof, to reduce the rate of fracture and/or increase the rate of fracture healing in mammals.

Another aspect of the invention is directed to the use of a compound of the formula (I), as a free base or a pharmaceutically acceptable salt thereof, to increase cancellous bone formation and/or new bone formation in mammals.

Another aspect of the invention is directed to a method of prevention and/or treatment of bone-related disorders comprising administering to a mammal in need of such prevention and/or treatment, a therapeutically effective amount of a compound of the formula (I) as a free base or a pharmaceutically acceptable salt thereof.

Another aspect of the invention is directed to a method of prevention and/or treatment of osteoporosis comprising administering to a mammal in need of such prevention and/or treatment, a therapeutically effective amount of a compound of the formula (I) as a free base or a pharmaceutically acceptable salt thereof.

Another aspect of the invention is directed to a method of increasing bone formation comprising administering to a mammal in need of such treatment, a therapeutically effective amount of a compound of the formula (I) as a free base or a pharmaceutically acceptable salt thereof.

Another aspect of the invention is directed to a method of increasing bone mineral density comprising administering to a mammal in need of such treatment, a therapeutically effective amount of a compound of the formula (I) as a free base or a pharmaceutically acceptable salt thereof.

Another aspect of the invention is directed to a method of reducing the incidence of fracture comprising administering to a mammal in need of such treatment, a therapeutically effective amount of a compound of the formula (I) as a free base or a pharmaceutically acceptable salt thereof.

Another aspect of the invention is directed to a method of enhancing fracture healing comprising administering to a mammal in need of such treatment, a therapeutically effective amount of a compound of the formula (I) as a free base or a pharmaceutically acceptable salt thereof.

Another aspect of the invention is directed to said methods and wherein said mammal is a human.

Another aspect of the invention is directed to said methods and wherein said mammal is a vertibrate animal, preferably but not limited to bigger animals such as horses, camels, dromedars but not limited thereto.

Compounds of formula (I) including the herein named are disclosed in WO 03/004472. The effect of the compounds of the present invention on bone growth has been investigated. It has been found that such compounds are well suited to promote and increase bone formation, increase bone mineral density and consequently for inhibiting bone-related disorders such as osteoporosis.

The use of the GSK3 inhibitors, the compounds of the formula (I), in primary and secondary ostopeorosis, where primary osteoporosis includes postmenopausal osteoporosis and senile osteoporosis in both men and women, and secondary osteoporosis includes cortison induced osteoporosis, as well as any other type of induced secondary osteoporosis, are included in the term osteoporosis. In addition to this, these GSK3 inhibitors may also be used in treatments of myeloma. These GSK3 inhibitors may be administered locally or systemically, in different formulation regimes, to treat these conditions.

The promotion and increasing of bone formation makes these compounds of the formula (I) suitable to reducing the incidence of fracture, to reduce the rate of fracture and/or increase the rate of fracture healing, to increase cancellous bone formation and/or new bone formation in mammals.

The use to promote and increase new bone formation may be in connection with surgery. This invention can be used during surgery, where the treating surgeon will place the invention locally in an appropriate formulation, near the deficient bone and/or in the body cavity. The bone may for instance have been broken, and utilizing the invention as described and claimed herein will then be placed in or near the fracture during open fracture repair. In some instances bone pieces may be missing (e.g. after tumour removal or severe casualties), and utilizing the invention as described and claimed herein will then be placed near the site of constructive bone surgery.

Another aspect of the invention is directed to implants for implantation into bone tissue having an improved rate of attachment between the implant and the bone tissue such that post-surgery healing periods are reduced and/or an immediate or early loading of the implant are enabled.

Another object of the invention is to provide an implant forming a mechanically stronger bond with bone tissue. Thus, an implant intended for implantation into bone tissue having an improved biocompatibility is to be provided.

As used herein the term "implant" includes within its scope any device or material together with formulation of the compound intended to be implanted into the body of a vertebrate animal, in particular a mammal, such as a human. Implants may be used to replace anatomy and/or restore any function of the body.

Generally, an implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

As used herein the term "implant (intended) for implantation into bone tissue" refers to implants intended for at least partial implantation into bone tissue, such as dental implants, orthopaedic implants, and the like. An implant for implantation into bone tissue may also be referred to as a bone tissue implant. Non-limiting examples of such implants are a prosthetic femoral hip joint; a prosthetic femoral head; a prosthetic acetabular cup; a prosthetic elbow, including implants adapted to replace a stem, a wedge, or an articular insert; a prosthetic knee, including implants adapted to replace a femoral component, a tibial component, a stem, a wedge, an articular insert or a patellar component; a prosthetic shoulder, including implants adapted to replace a stem or a head; a prosthetic wrist; a prosthetic ankle; a prosthetic hand; a prosthetic finger; a prosthetic toe; a prosthetic vertebrae; a prosthetic spinal disc; a prosthetic heart valve; a pacemaker; a catheter; a prosthetic vessel; a space filling implant; an implant for retention of a hearing aid; an implant for external fixation; an intrauterine device (IUDs); a bioelectronic device, including intracochlear and intracranial electronic devices; an artificial joint; a dental implant; an orthopaedic implant; an ossiculoplastic implant; a middle ear implant, including implants adapted to replace an incus, a malleus, a stapes, an incus-stapes, a malleus-incus, or a malleus-incus-stapes; a cochlear implant; and an orthopaedic fixation device, including a nail, a screw, a staple or a plate.

As used herein the term "implant surface" refers to at least one defined surface region of an implant. Thus, the defined surface region may include the entire surface area of the implant or portions thereof.

An example of an implant surface intended for implantation into bone tissue is the surface of a dental fixture that is intended for implantation into the jawbone of a patient and to be in contact with bone tissue.

Another example of an implant surface intended for implantation into bone tissue is the surface of a hip joint implant that is intended for implantation into the neck of the femur of a patient.

It is essential that the implant establish a sufficient stability and bond between implant and bone tissue to enable the above disclosed immediate or early loading of the implant. It shall also be noted that an immediate or early loading of the implant may be beneficial to bone formation.

Some of the metals or alloys, such as titanium, zirconium, hafnium, tantalum, niobium, or alloys thereof, that are used for bone implants are capable of forming a relatively strong bond with the bone tissue, a bond which may be as strong as the bone tissue per se, sometimes even stronger. This bond between the metal and the bone tissue has been termed "osseointegration" by Bränemark et al. Acta Orthop Scand, 1981, 52, 155-170. Although the bond between the metal, e.g. titanium, and the bone tissue may be comparatively strong, it is desirable to enhance this bond.

Thus, one aspect of the invention is directed to implants treated with a compound of the formula (I), as a free base or a pharmaceutically acceptable salt thereof or a composition including such a compound. One aspect of the invention is directed to metallic implants. Another aspect of the invention is directed to metallic implants, which are made of commercially pure titanium or alloy of titanium. Another aspect of the invention is a dental implant and an orthopaedic implant.

Examples of compounds useful in treating implants are without limitation compounds of the formula (I), such as 3-amino-6-[4-(4-methylpiperazin-1-yl)sulfonylphenyl]-N-pyridin-3-ylpyrazine-2-carboxamide;

3-amino-6-(4-piperazin-1-ylsulfonylphenyl)-N-pyridin-3-ylpyrazine-2-carboxamide;

3-amino-N-pyridin-3-yl-6-(4-sulfamoylphenyl)pyrazine-2-carboxamide;

3-amino-6-[2,5-difluoro-4-(4-methylpiperazin-1-yl)sulfonyl-phenyl]-N-pyridin-3-yl-pyrazine-2-carboxamide;

3-amino-6-[3-ethyl-4-(4-methylpiperazin-1-yl)sulfonyl-phenyl]-N-pyridin-3-yl-pyrazine-2-carboxamide;

3-amino-6-[3-fluoro-4-(4-methylpiperazin-1-yl)sulfonyl-phenyl]-N-pyridin-3-yl-pyrazine-2-carboxamide;

3-amino-6-[3-methyl-4-(4-methylpiperazin-1-yl)sulfonyl-phenyl]-N-pyridin-3-yl-pyrazine-2-carboxamide;

3-amino-6-[2-methyl-4-(4-methylpiperazin-1-yl)sulfonyl-phenyl]-N-pyridin-3-yl-pyrazine-2-carboxamide;

3-amino-6-[4-(4-methylpiperazin-1-yl)sulfonyl-3-(trifluoromethoxy)phenyl]-N-pyridin-3-yl-pyrazine-2-carboxamide;

3-amino-6-[4-(4-methylpiperazin-1-yl)sulfonyl-2-(trifluoromethyl)phenyl]-N-pyridin-3-yl-pyrazine-2-carboxamide;

3-amino-6-[5-fluoro-2-methyl-4-(4-methylpiperazin-1-yl)sulfonyl-phenyl]-N-pyridin-3-yl-pyrazine-2-carboxamide;

3-amino-6-[2,5-dimethyl-4-(4-methylpiperazin-1-yl)sulfonyl-phenyl]-N-pyridin-3-yl-pyrazine-2-carboxamide;

3-amino-6-[2-fluoro-4-(4-methylpiperazin-1-yl)sulfonyl-phenyl]-N-pyridin-3-yl-pyrazine-2-carboxamide;

3-amino-6-[4-(4-ethylpiperazin-1-yl)sulfonylphenyl]-N-pyridin-3-yl-pyrazine-2-carboxamide and 3-amino-6-[4-[(4-methyl-1,4-diazepan-1-yl)sulfonyl]phenyl]-N-pyridin-3-yl-pyrazine-2-carboxamide, as a free base or a pharmaceutically acceptable salt thereof.

The compounds used in accordance with the present invention may have chiral centres and/or geometric isomeric centres (E- and Z-isomers), and it is to be understood that the invention encompasses uses of also such optical, diastereoisomers and geometric isomers.

The invention further encompasses the use of any and all tautomeric forms of a compound of the formula (I).

A suitable pharmaceutically acceptable salt of the compound useful in accordance to the invention is, for example, an acid-addition salt, which is sufficiently basic, for example an inorganic or organic acid. In addition a suitable pharmaceutically acceptable salt of the compounds of the invention, which is sufficiently acidic, is an alkali metal salt, an alkaline earth metal salt or a salt with an organic base, which affords a physiologically-acceptable cation.

The compound of the formula (I) or salt thereof, may be prepared as described in WO 03/004472, which hereby is incorporated by reference.

Pharmaceutical Composition

The composition used in accordance with the present invention may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream, for rectal administration as a suppository and for local administration in a body cavity or in a bone cavity as an implant or on the implant surface. The composition can be incorporated in and/or associated with (physically and/or chemically) the surface of the implant, or administrated separately (before, at the same time or after) with regard to the implant in the body cavity or bone cavity.

The composition can be incorporated in and/or associated with the implant surface using any suitable method, such as:

plasma deposition of the substance onto the implant, any electrochemical treatment involving the substance, e.g. anodisation of the implant in an electrolyte comprising the substance, treatment of the implant with an aqueous and/or non-aqueous solution comprising the substance, e.g. by dipping the implant in said solution, treatment of the implant with a sol-gel technique involving the substance, or any combination of these methods or the like.

In general the above described compositions may be prepared in a conventional manner using pharmaceutically acceptable carriers or diluents.

Suitable daily doses of the compounds of the formula (I) used in the treatment of a mammal, including human, are approximately from about 0.01 to 250 mg/kg bodyweight at peroral administration and from about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

Illustrative representative pharmaceutical dosage forms containing the compounds of the formula (I), including 3-amino-6-{4-[(4-methylpiperazin-1-yl)sulfonyl]phenyl}-N-pyridin-3-ylpyrazine-2-carboxamide, 3-amino-6-(4-piperazin-1-ylsulfonylphenyl)-N-pyridin-3-ylpyrazine-2-carboxamide or 3-amino-N-pyridin-3-yl-6-(4-sulfamoylphenyl)pyrazine-2-carboxamide as a free base or a salt thereof, are described in WO 03/004472, which dosage forms are hereby incorporated by reference.

For veterinary use the amounts of different components, the dosage form and the dose of the medicament may vary and will depend on various factors such as, for example the individual requirement of the animal treated.

It has been found that bone formation and bone mineral density can be increased by the uses of compounds of the formula (I) above. The term "therapy" as used in accordance with the invention also includes "prevention" unless there are specific indications to the contrary. The terms "therapeutic" and "therapeutically" should be construed accordingly.

EXAMPLES

The invention is now described below by the non-limiting examples:

Example 1

Increased Bone Formation in Rats Treated with 3-amino-6-[4-(4-methylpiperazin-1-yl)sulfonylphenyl]-N-pyridin-3-ylpyrazine-2-carboxamide The compound 3-amino-6-[4-(4-methylpiperazin-1-yl)sulfonylphenyl]-N-pyridin-3-ylpyrazine-2-carboxamide was formulated as a solution in water. Male and female Han Wistar rats were dosed by oral gavage, at dosages of 10, 30 or 60 μmol/kg/day for four weeks and compared to vehicle controls. Complete necropsies were performed and the tissues preserved in 10% formalin. The femur, femorotibial joint, sternum and hind paws were decalcified, embedded in paraffin, sectioned at 5 μm thickness and stained with hematoxylin and eosin. As evaluated by light microscopy, increased bone formation in the form of thickened trabeculae, thickened cortical bone, periosteal hyperostosis and increased number of osteoblasts occurred at all dose levels (FIG. 1b).

Figure 1A:
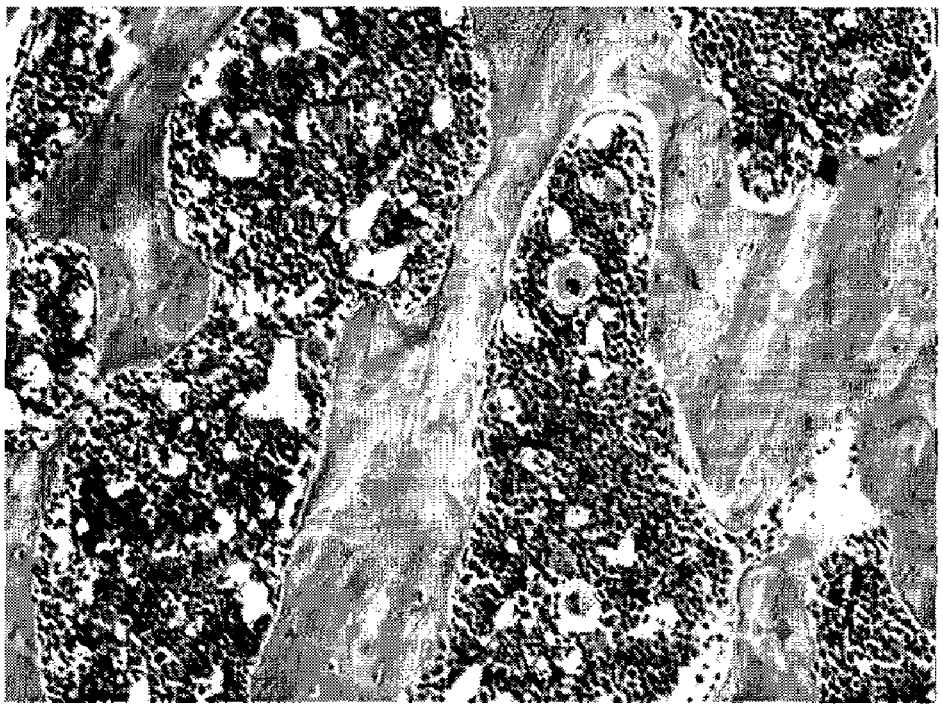
FIG. 1a shows normal trabeculae and bone marrow in the femur (diaphysis) of a vehicle-treated control rat.

FIG. 1a shows normal trabeculae and bone marrow in the femur (diaphysis) of a vehicle-treated control rat. FIG. 1b shows a marked increase in formation of osteoid in the same area of the femur in a rat treated with 60 μmol/kg of 3-amino-6-[4-(4-methylpiperazin-1-yl)sulfonylphenyl]-N-pyridin-3-ylpyrazine-2-carboxamide for 4 weeks. (magnification: ×100).

Example 2

Increased Osteocalcin, Parathyroid Hormone (PTH) and Calcitonin Levels in Rats Treated with 3-amino-6-[4-(4-methylpiperazin-1-yl)sulfonylphenyl]-N-pyridin-3-ylpyrazine-2-carboxamide In a separate rat study, the effect of the compound 3-amino-6-[4-(4-methylpiperazin-1-yl)sulfonylphenyl]-N-pyridin-3-ylpyrazine-2-carboxamide on osteocalcin levels, used as a marker for bone formation, was studied. Parathyroid hormone (PTH) and calcitonin levels were also analysed. The compound was formulated as a solution in water. Male Sprague Dawley rats were given 30 μmol/kg/day of the compound orally for 7 days and then compared to vehicle control rats. Blood samples were taken before the first drug administration at day 1, and 3 hours after the last dose at day 7. Osteocalcin plasma levels were measured using a commercial immunoassay (ELISA kit (catalogue # BT-490, Biomedical Technologies Inc. MA, USA)). Intact PTH levels were analyzed using a commercial ELISA kit (catalogue # 60-2700, Immutopics Inc. CA, USA). The calcitonin was measured in the following way, 200 μL plasma was precipitated with 1 mL acid ethanol, mixed vigorously and centrifuged for 15 min at 1500 g. The supernatant was decanted into a new tube and evaporated with a stream of nitrogen in a Turbo Vap. After reconstitution in assay buffer, calcitonin levels were analyzed using a commercial ELISA kit (catalogue # S-1197, Peninsula. Calif., USA).

Osteocalcin as well as PTH and calcitonin plasma levels were significantly increased in the drug-treated rats (FIGS. 2-4). The increased PTH and calcitonin levels reflect the need for calcium in the mineralisation of the newly formed bone. Histopathologically, increased bone formation of a similar character as previously observed (Example 1, FIG. 1b) was present in the drug-treated rats.

Example 3

Increased Bone Formation in Rats Treated with 3-amino-6-[4-(4-methylpiperazin-1-yl)sulfonylphenyl]-N-pyridin-3-ylpyrazine-2-carboxamide In a separate rat study, the effect of the compound 3-amino-6-[4-(4-methylpiperazin-1-yl)sulfonylphenyl]-N-pyridin-3-ylpyrazine-2-carboxamide on the bone mineral density (BMD) was measured in rat plasma in nM. The compound was formulated as a ultrapure solution in water (pH 3.5). The Male Sprague Dawley rats were dosed during 14 days by oral gavage. The study contained 4 dose groups with different dosing regimes and a vehicle control, namely 3 μmol/kg (twice daily) or 30 μmol/kg (once daily, once every second day or once every fourth day). Plasma samples were always taken 2 hrs after the oral dose was given in the morning. After 14 days, the rats were euthanized, and their right femurs were removed. The trabecular bone density of the femur metaphyses were measured utilizing peripheral quantitative computed Tomography method. The results are shown in FIG. 5a, that shows the BMD increases (bone mineral density increases) in mg per cubic centimeter on the Y-axis, that occur in the trabeculae of the right femur metaphysis. The X axis displays the plasma concentrations (+/−Standard Deviation) of 3-amino-6-[4-(4-methylpiperazin-1-yl)sulfonylphenyl]-N-pyridin-3-ylpyrazine-2-carboxamide.

Example 4

Increased Bone Formation in Rats Treated 3-amino-6-(4-piperazin-1-ylsulfonylphenyl)-N-pyridin-3-ylpyrazine-2-carboxamide The effect of the compound 3-amino-6-(4-piperazin-1-yl-sulfonylphenyl)-N-pyridin-3-ylpyrazine-2-carboxamide on the bone mineral density (BMD) was measured in rat plasma in nM in an analogous way as described in Example 3 above. The results are shown in FIG. 5b, that shows the BMD increases (bone mineral density increases) in mg per cubic centimeter, that occur in the trabeculae of the right femur metaphysic.

Example 5

Increased Bone Formation in Rats Treated with 3-amino-N-pyridin-3-yl-6-(4-sulfamoylphenyl)pyrazine-2-carboxamide The effect of the compound 3-amino-N-pyridin-3-yl-6-(4-sulfamoylphenyl)pyrazine-2-carboxamide on the bone mineral density (BMD) was measured in rat plasma in nM in an analogous way as described in Example 3 above. The results are shown in FIG. 5c, that shows the BMD increases (bone mineral density increases) in mg per cubic centimeter, that occur in the trabeculae of the right femur metaphysic.

The invention claimed is:

1. A method of treatment of bone-related disorders comprising administering to a mammal in need thereof a therapeutically effective amount of 3-amino-6-[4-(4-methylpiperazin-1-yl)sulfonylphenyl]-N-pyridin-3-ylpyrazine-2-carboxamide.

2. A method of treatment of osteoporosis comprising administering to a mammal a therapeutically effective amount of 3-amino-6-[4-(4-methylpiperazin-1-yl)sulfonylphenyl]-N-pyridin-3-ylpyrazine-2-carboxamide.

3. A method of increasing bone formation comprising administering to a mammal a therapeutically effective amount of 3-amino-6-[4-(4-methylpiperazin-1-yl)sulfonylphenyl]-N-pyridin-3-ylpyrazine-2-carboxamide.

4. A method of increasing cancellous bone formation and/or new bone formation comprising administering to a mammal a therapeutically effective amount of 3-amino-6-[4-(4-methylpiperazin-1-yl)sulfonylphenyl]-N-pyridin-3-ylpyrazine-2-carboxamide.

5. A method of increasing bone mineral density comprising administering to a mammal a therapeutically effective amount of 3-amino-6-[4-(4-methylpiperazin-1-yl)sulfonylphenyl]-N-pyridin-3-ylpyrazine-2-carboxamide.

6. A method of reducing the incidence of fracture comprising administering to a mammal a therapeutically effective amount of 3-amino-6-[4-(4-methylpiperazin-1-yl)sulfonylphenyl]-N-pyridin-3-ylpyrazine-2-carboxamide.

7. A method of enhancing fracture healing comprising administering to a mammal, a therapeutically effective amount of 3-amino-6-[4-(4-methylpiperazin-1-yl)sulfonylphenyl]-N-pyridin-3-ylpyrazine-2-carboxamide.

8. A method according to claim 1, wherein said mammal is a human.

9. A method according to claim 2, wherein said mammal is a human.

10. A method according to claim 3, wherein said mammal is a human.

11. A method according to claim 4, wherein said mammal is a human.

12. A method according to claim 5, wherein said mammal is a human.

13. A method according to claim 6, wherein said mammal is a human.

14. A method according to claim 7, wherein said mammal is a human.

* * * * *